United States Patent
O'Halloran et al.

(10) Patent No.: US 9,526,550 B2
(45) Date of Patent: Dec. 27, 2016

(54) METHODS AND APPARATUS FOR TREATING VERTEBRAL FRACTURES

(71) Applicant: GLOBUS MEDICAL, INC, Audubon, PA (US)

(72) Inventors: Damien O'Halloran, Conshohocken, PA (US); David C Paul, Phoenixville, PA (US); Sean Suh, Plymouth Meeting, PA (US)

(73) Assignee: Globus Medical, Inc., Audubon, PA (US)

( * ) Notice: Subject to any disclaimer, the term of this patent is extended or adjusted under 35 U.S.C. 154(b) by 230 days.

(21) Appl. No.: 14/254,614

(22) Filed: Apr. 16, 2014

(65) Prior Publication Data

US 2014/0303633 A1  Oct. 9, 2014

Related U.S. Application Data

(63) Continuation of application No. 12/632,325, filed on Dec. 7, 2009, now Pat. No. 8,734,458.

(51) Int. Cl.
*A61B 17/88* (2006.01)
*A61B 17/70* (2006.01)

(52) U.S. Cl.
CPC ....... *A61B 17/8802* (2013.01); *A61B 17/7097* (2013.01); *A61B 17/8811* (2013.01); *A61B 17/8855* (2013.01)

(58) Field of Classification Search
CPC .................. A61B 17/7097; A61B 17/8855
See application file for complete search history.

(56) References Cited

U.S. PATENT DOCUMENTS

2004/0098015 A1* 5/2004 Weikel ................ A61B 17/025
                                                              606/192
2009/0299374 A1* 12/2009 Tilson ................ A61B 17/8816
                                                              606/94

* cited by examiner

*Primary Examiner* — David Bates
*Assistant Examiner* — Olivia C Chang

(57) ABSTRACT

Methods and apparatus for treating bones, including, in one or more embodiments, methods and apparatus for treatment of vertebral fractures that include an inflation device for cavity creation and an inflation and containment device for maintaining vertebral height and cement containment. Methods for treating a bone comprising: creating a cavity in the bone; inflating a containment jacket in the cavity; inflating a balloon within the containment jacket so that the balloon occupies a first portion of the containment jacket; introducing a first filler material into a second portion of the containment jacket, wherein the second portion of the containment jacket is not occupied by the balloon; removing the balloon from the containment jacket; and introducing a second filler material into the first portion of the containment jacket.

9 Claims, 7 Drawing Sheets

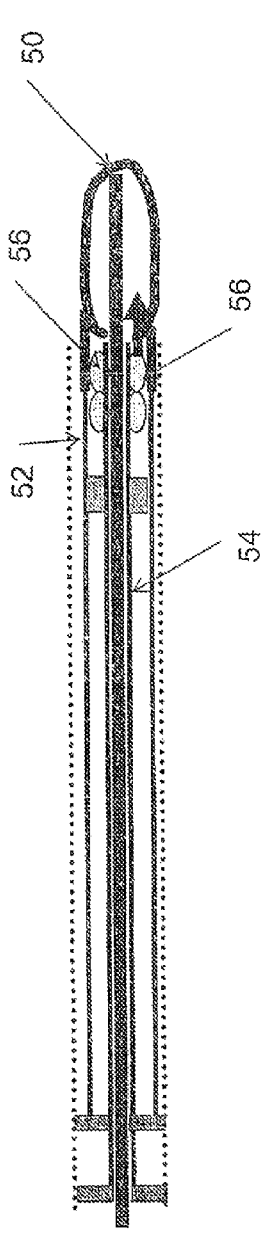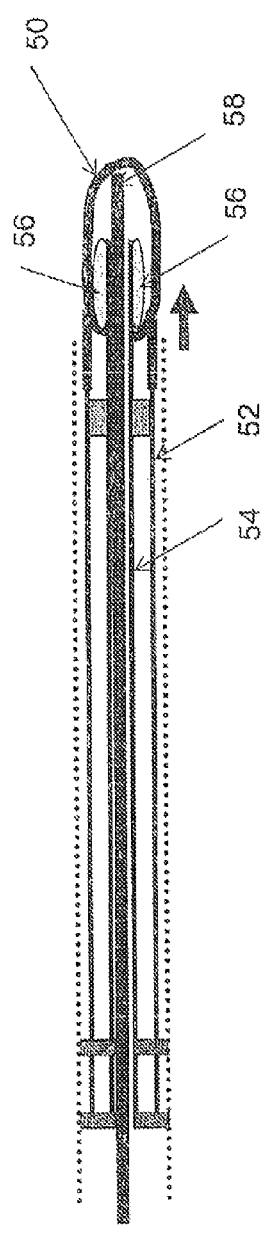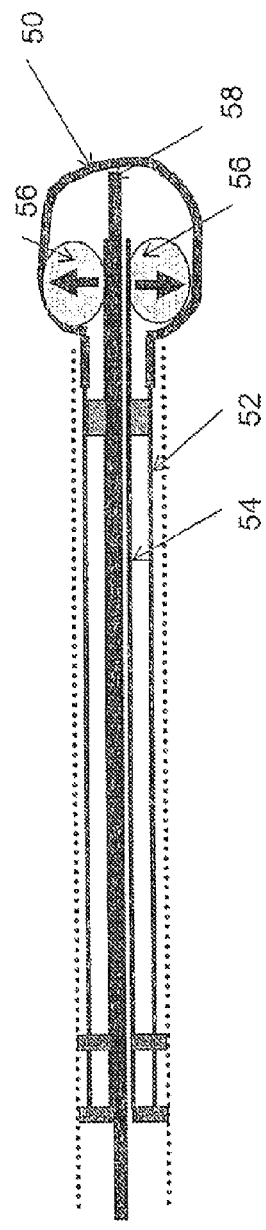

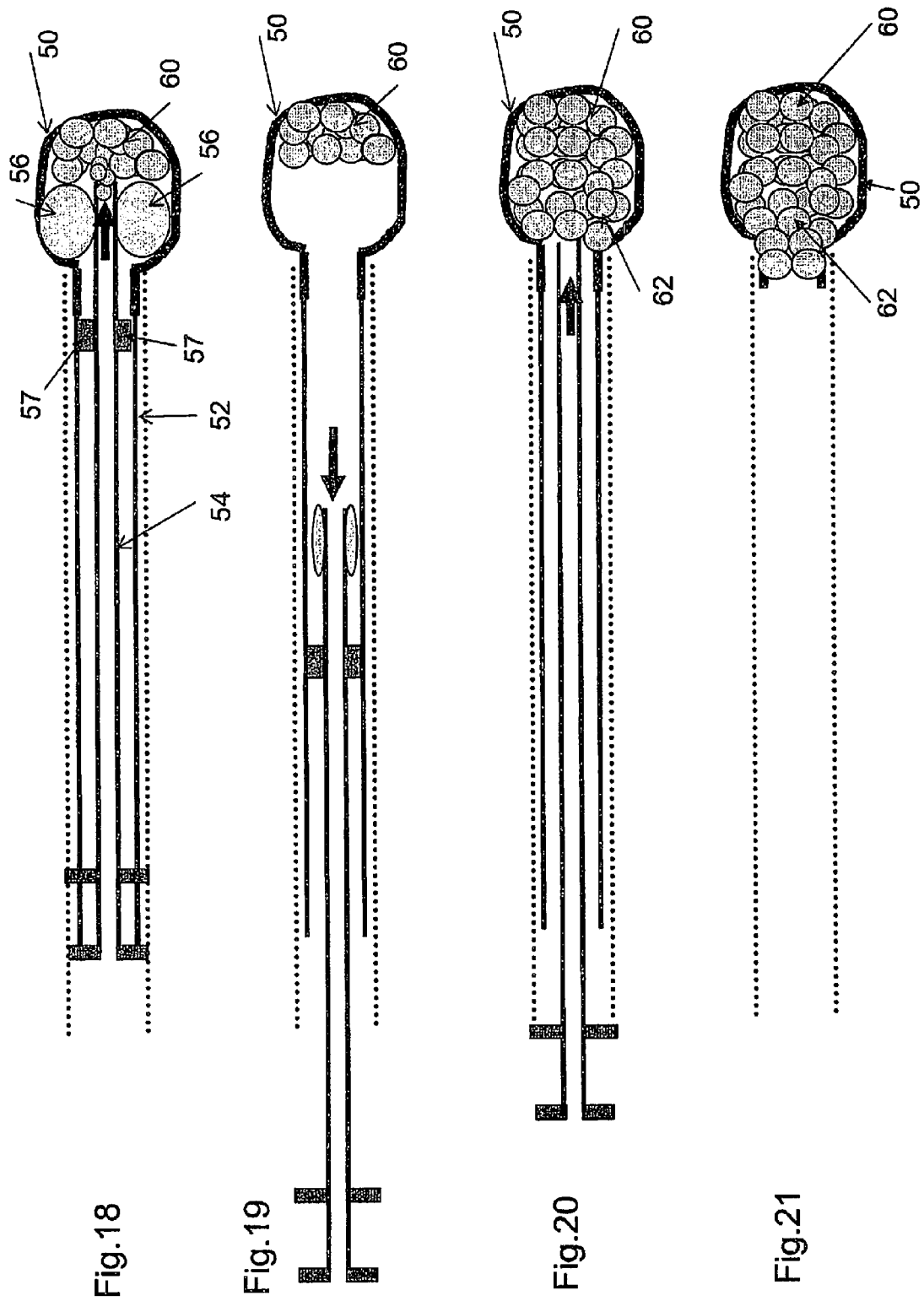

METHODS AND APPARATUS FOR TREATING VERTEBRAL FRACTURES

CROSS REFERENCE TO RELATED APPLICATIONS

This application is a continuation of U.S. patent application Ser. No. 12/632,325, filed on Dec. 7, 2009, which is incorporated by reference in its entirety herein.

FIELD OF THE INVENTION

The present disclosure generally relates to treatment of bones. In particular, in one or more embodiments, the present disclosure relates to methods and apparatus for treatment of vertebral fractures that include an inflation device for cavity creation and an inflation and containment device for maintaining vertebral height and cement containment.

BACKGROUND

Bones and bony structures are susceptible to a variety of weaknesses that can affect their ability to provide support and structure. Weaknesses in bony structures may have many causes, including degenerative diseases, tumors, fractures, and dislocations. By way of example, weaknesses in vertebrae from lead to compression fractures that involve the collapse of one or more vertebrae in the spine. These vertebral compression fractures may be caused by a number of conditions including osteoporosis, trauma, and tumors. Advances in medicine and engineering have provided doctors with a plurality of devices and techniques for alleviating or curing these weaknesses.

One technique for treating vertebral fractures is vertebroplasty. In vertebroplasty, a physician may use a needle to inject bone cement into a fractured vertebral body to stabilize the fracture. Kyphoplasty is another technique for treating vertebra fractures that involves insertion of a balloon into the fractured vertebra to create a bone cavity in the vertebra. The balloon may then be removed followed by injection of bone cement into the vertebral body to stabilize the fracture. Leakage of the bone cement in both vertebroplasty and kyphoplasty is a common problem that can lead to complications. Another problem associated with these techniques is the potential for inadequate height restoration to the fractured vertebral body.

Thus, there is a need for methods and apparatus that can provide stabilization to a fractured vertebra.

SUMMARY

The present disclosure generally relates to treatment of bones. In particular, in one or more embodiments, the present disclosure relates to methods and apparatus for treatment of vertebral fractures that includes a device for cavity creation, an inflation device and a containment device for maintaining vertebral height and cement containment.

An embodiment of the present invention includes a method for treating a bone. The method may comprise creating a cavity in the bone. The method further may comprise placing a containment jacket in the cavity. The method further may comprise inflating a balloon within the containment jacket so that the balloon occupies a first portion of the containment jacket. The method further may comprise introducing a first filler material into a second portion of the containment jacket, wherein the second portion of the containment jacket is not occupied by the balloon. The method further may comprise removing the balloon from the containment jacket. The method further may comprise introducing a second filler material into the first portion of the containment jacket.

The features and advantages of the present invention will be readily apparent to those skilled in the art. While numerous changes may be made by those skilled in the art, such changes are within the spirit of the invention.

BRIEF DESCRIPTION OF THE DRAWINGS

FIGS. 15-21 illustrate yet another embodiment of a system and method for treating vertebral fractures.

DETAILED DESCRIPTION OF THE ILLUSTRATED EMBODIMENTS

The present disclosure generally relates to treatment of bones. In particular, in one or more embodiments, the present disclosure relates to methods and apparatus for treatment of vertebral fractures that include an inflation device for cavity creation and an inflation and containment device for maintaining vertebral height and cement containment.

Figure 1:
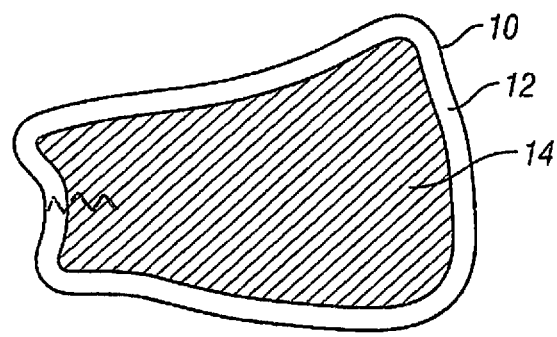
FIG. 1 is a cross-sectional view of a vertebral body in accordance with one embodiment of the present technique.

FIG. 1 illustrates a vertebral body 10 having a compression fracture therein with associated loss of height. As illustrated, the vertebral body 10 includes an exterior portion of cortical bone 12 and an interior portion of cancellous bone 14.

Figure 2:
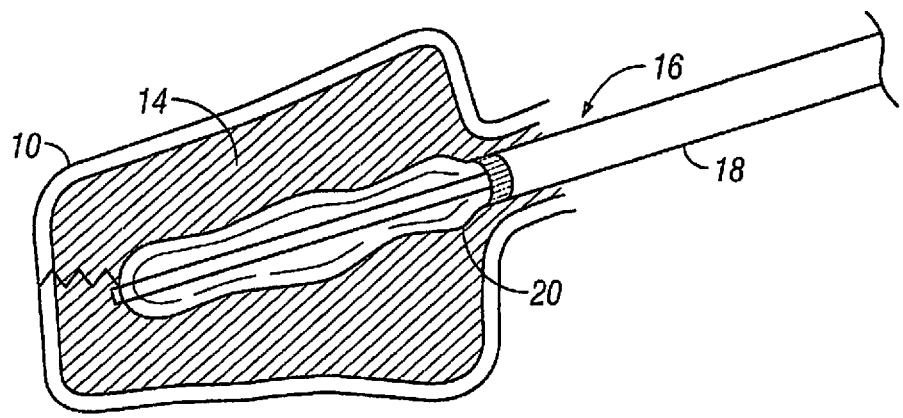
FIG. 2 illustrates an inflation device inserted into a vertebral body in accordance with one embodiment of the present invention.
Figure 3:
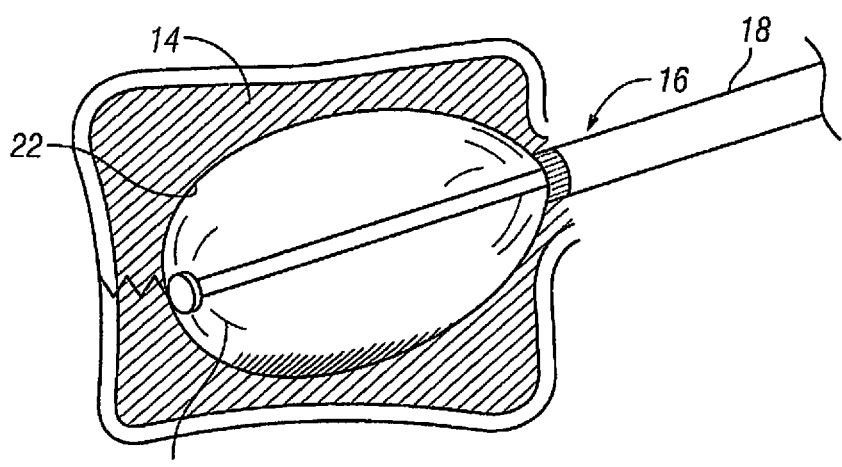
FIG. 3 illustrates employment of an inflation device to create a cavity in a vertebral body in accordance with one embodiment of the present invention.
Figure 4:
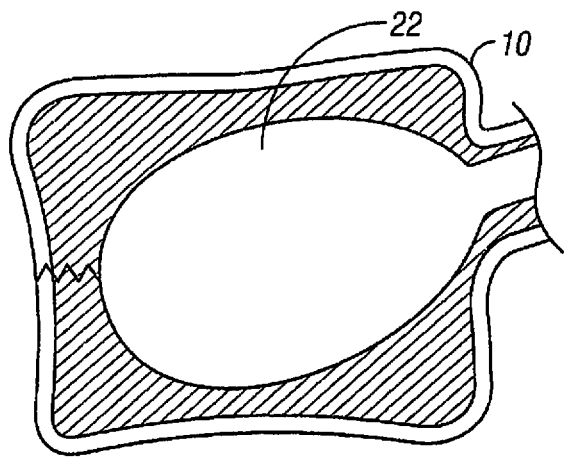
FIG. 4 illustrates a cavity created in a vertebral body in accordance with one embodiment of the present invention.

FIGS. 2-4 illustrate creation of a cavity in the vertebral body 10, in accordance with one embodiment of the present invention. As illustrated in FIG. 2, an inflation device 16 may be inserted into the cancellous bone 14 of the vertebral body 10. In the illustrated embodiment, the inflation device 16 includes a fill tube 18 and a first balloon 20 on the distal end of the fill tube 18. As illustrated, the first balloon 20 may be deflated when the inflation device 16 is inserted into the vertebral body 10. In certain embodiments, the inflation device 16 may be an inflatable bone tamp. It should be understood that the passageway into the vertebral body 10 for the inflation device 16 may be created using any of a variety of different suitable techniques. While not illustrated, a trocar, for example, may be used to place a cannula into the patient's body. A drill may then be inserted into the cannula, for example, and used to create a channel into the vertebral body 10 into which the inflation device 16 may be inserted. The inflation device 16 may then be inserted through the cannula into the vertebral body 10, for example.

FIG. 3 illustrates employment of the inflation device 16 to create a cavity 22 in the vertebral body 10, in accordance with one embodiment of the present invention. As illustrated, the first balloon 20 may inflate, for example, to compact the cancellous bone 14 in the interior portion of the vertebral body 10. In addition to creation of the cavity 22, the first balloon 20 may also, for example, force apart the compact bone 12, restoring height to the vertebral body 10. The inflation device 16 may then be removed from the vertebral body 10. While FIG. 3 illustrates the use of the first balloon 20 for creation of the cavity 22, those of ordinary skill in the art will appreciate that other suitable techniques may also be used for creation of the cavity 22. By way of example, an expandable jack or other suitable device may be used to create the cavity 22 in the vertebral body 10.

FIG. 4 illustrates the cavity 22 that has been created in the vertebral body 10 after removal of the inflation device 16, in accordance with embodiments of the present invention. While not illustrated, embodiments of the present invention further may include coating the wall of the cavity 22 with a bone growing agent, or a hemostatic sealing agent.

Figure 5:
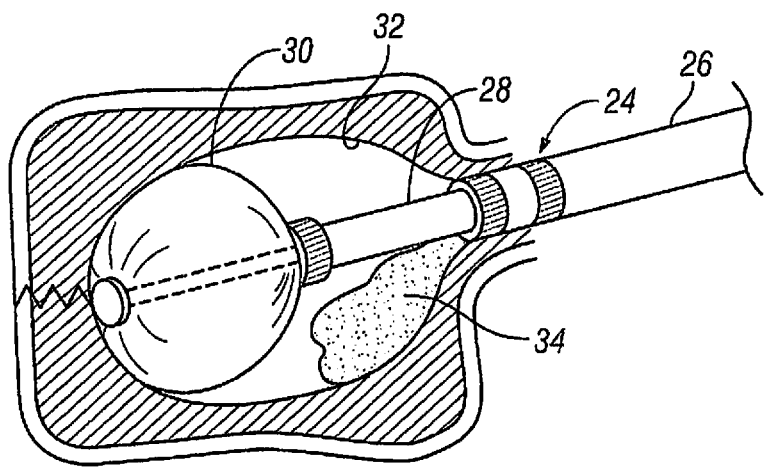
FIG. 5 illustrates employment of an inflation and containment device in a vertebral body in accordance with one embodiment of the present invention.

FIG. 5 illustrates employment of an inflation and containment device 24 in the vertebral body, in accordance with embodiments of the present invention. As illustrated, the inflation and containment device 24 may be inserted into the cavity 22 in the vertebral body 10. In certain embodiments, a second inflation device may be inserted into the vertebral body 10 through a cannula (not illustrated). In the illustrated embodiment, the inflation and containment device 24 includes an exterior tube 26, an interior fill tube 28, a second balloon 30, and a containment jacket 32. As will be discussed in more detail below, the second balloon 30 may be employed to maintain the height of the vertebral body 10 while the cavity 22 is partially filled with a first volume 34 of a filler material. The containment jacket 32 may be employed to contain a filler material (e.g., cement) introduced into the cavity 22 to prevent undesirable leakage. In this manner, problems associated with leakage of the filler material from the cavity 22 and loss of vertebral height may be reduced or possibly even avoided.

The second balloon 30 may be located on a distal end or proximal end of the interior fill tube 28, in accordance with embodiments of the present invention. In certain embodiments, the second balloon 30 and interior fill tube 28 may be an inflatable bone tamp. While not illustrated, the second balloon 30 is deflated when the inflation and containment device 24 is inserted into the vertebral body 10. After insertion into the cavity 22, the second balloon 30 may then be inflated. In general, inflation of the second balloon 30 should provide pressure on the walls of the cavity 22 to prevent (or reduce) loss of vertebral height. It may be desirable, in certain embodiments, for expansion of the second balloon 30 to further increase the height of the vertebral body 10. In certain embodiments, inflation of the second balloon 30 may restore some vertebral height lost after removal of the first balloon 20. As illustrated, the second balloon 30 generally may be enclosed within the containment jacket 32. The volume of the second balloon 30 generally should be smaller than the volume of the containment jacket 32, in accordance with embodiments of the present invention. Furthermore, when inflated, the second balloon 30 generally should not occupy the entire volume of the containment jacket 32. By way of example, the second balloon 30 may occupy from about 10% to about 90% by volume of the containment jacket 32.

The containment jacket 32 may be located on a distal end of the exterior tube 26, in accordance with embodiments of the present invention. As illustrated, the containment jacket 32 may be attached to the distal end of the exterior tube 26 such that the containment jacket 32 encloses the distal end of the exterior tube 26. While not illustrated, the containment jacket 32 may be deflated when the inflation and containment device 24 is inserted into the vertebral body 10. After insertion into the cavity 22, the containment jacket 32 may be inflated as the second balloon within the containment jacket is inflated. As illustrated, the containment jacket 32 may conform to the shape of the cavity 22. In certain embodiments, the volume of the containment jacket 32 may be larger than the volume of the cavity 22. It may be desirable, in certain embodiments, for the containment jacket 32 to be a compliant balloon (e.g., polyurethane) that can contain the filler material to prevent leakage. Accordingly, the containment jacket may permit interdigitation of the filler material with the cancellous bone, in accordance with embodiments of the present invention.

As illustrated by FIG. 5, employment of the inflation and containment device 24 includes inflation of the containment jacket 32 and inflation of the second balloon 30, in accordance with embodiments of the present technique. As further illustrated by FIG. 5, the cavity 22 may then be partially filled with a first cement volume 34. In the illustrated embodiment, the first cement volume 34 may be introduced into the containment jacket 32, for example, by way of the exterior tube 26. The first cement volume 34 generally may fill the portion of the containment jacket 32 that is not occupied by the inflated second balloon 30. By way of example, the first cement volume 34 may occupy from about 10% to about 90% by volume of the containment jacket 32 as inflated in the cavity 22. The first cement volume 34 may then be allowed to cure in the containment jacket 32. After the first cement volume 34 has substantially cured, the second balloon 30 may be removed from the cavity.

Figure 6:
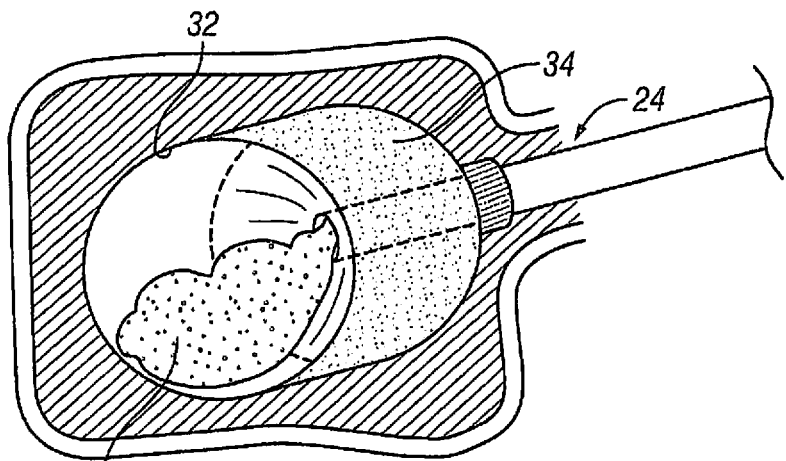
FIG. 6 illustrates further employment of an inflation and containment device in a vertebral body in accordance with one embodiment of the present invention.

FIG. 6 illustrates further employment of the inflation and containment device 24 in accordance with embodiments of the present invention. As previously mentioned, the second balloon 30 may be removed from the cavity 22 after the first cement volume 34 has substantially cured. In the illustrated embodiment, the containment jacket 32 remains in the cavity 22. As illustrated, a second cement volume 36 may then be introduced into the containment jacket 32. The second cement volume 36 generally may occupy the unoccupied portion of the containment jacket 32, for example, the portion of the containment jacket 32 that is not occupied by the first volume 32 of cement. By way of example, the second cement volume 36 may occupy from about 10% to about 90% by volume of the containment jacket 32 as inflated in the cavity 22. The second cement volume 36 may then be allowed to cure in the containment jacket 32. The inflation and containment device 24 may then be removed from the vertebral body 10. In accordance with embodiments of the present invention, the containment jacket 32 may be detached from the device 24 and remain in the vertebral body 10.

Figure 7:
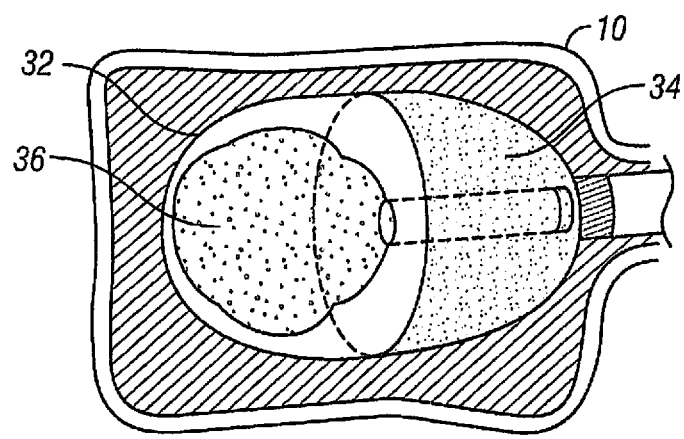
FIG. 7 illustrates a stabilized vertebral body in accordance with one embodiment of the present invention.

FIG. 7 illustrates the vertebral body 10 after stabilization of the compression fracture therein in accordance with embodiments of the present invention. As illustrated, the containment jacket 32 remains in the vertebral body 10 generally filling the cavity 22. The first cement volume 34 and the second cement volume 36 generally fill the containment jacket 32. As is readily apparent from a comparison of FIG. 7 and FIG. 1, height may be restored to the vertebral body 10 in accordance with embodiments of the present invention.

While the preceding description of FIGS. 5-7 describes the use of the inflation and containment device 24, it should be understood that the inflation and containment device 24 is an illustration of one device for maintaining vertebral height and cement containment in accordance with embodiments of the present technique. Other suitable devices for maintaining vertebral height and cement containment may also be used in present embodiments.

Figure 8:
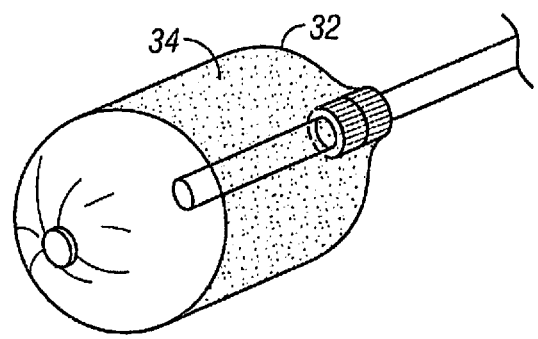
FIG. 8 illustrates a containment jacket in accordance with one embodiment of the present invention.
Figure 9:
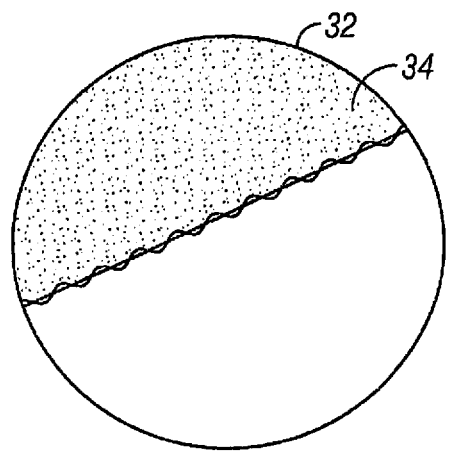
FIG. 9 is a close-up view of a containment jacket in accordance with one embodiment of the present invention.

FIGS. 8-9 illustrate the containment jacket 32 in accordance with one embodiment of the present invention. FIG. 9 is a close-up view of the containment jacket 32 in accordance with one embodiment of the present invention. As illustrated, the outer surface of the containment jacket 32 may be coated with a bone growing agent. The bone growing agent may be any of a variety of different materials suitable for promoting growth of the cancellous bone 14 that is adjacent to the containment jacket 32 in the vertebral body 10.

Figure 10:
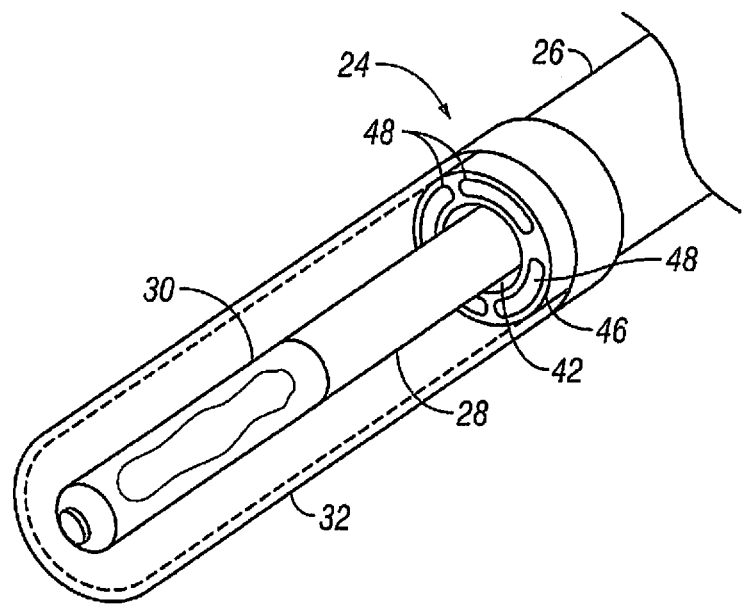
FIGS. 10 and 11 illustrate an inflation and containment device in accordance with one embodiment of the present invention.
Figure 11:
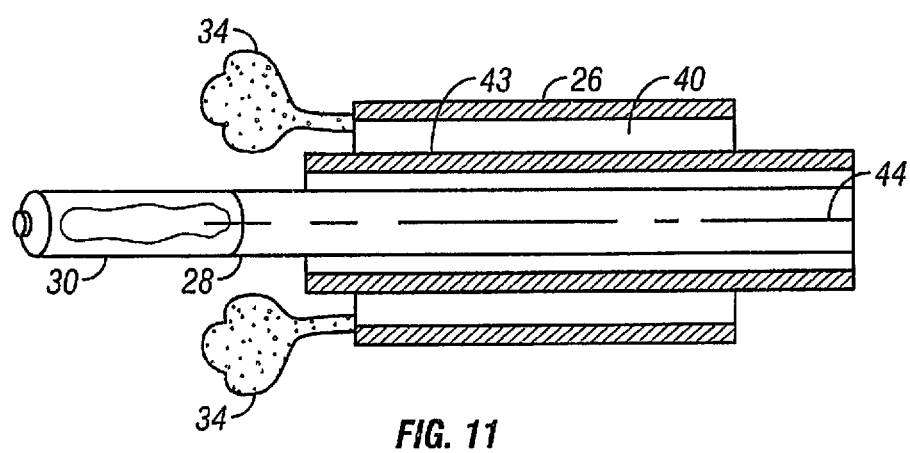

FIGS. 10-11 illustrate an inflation and containment device 24 that may be used in accordance with one embodiment of the present invention. As previously mentioned, the device 24 may be inserted into a vertebral body 10. As illustrated, the inflation and containment device 24 may comprise an exterior tube 26, an interior fill tube 28, a second balloon 30 in a deflated state, and a containment jacket 32. In the illustrated embodiment, the exterior tube 26 is a dual-duct tube that comprises an exterior passageway 40 an interior passageway 42. The exterior passageway may surround the interior passageway 42 with the passageways separated by an interior wall 43. Both the exterior passageway 40 and the interior passageway 42 may, for example, extend along the longitudinal axis 44 of the exterior tube. As illustrated, the distal end 46 of the exterior tube 26 may include one or more exit ports 48 for the exterior passageway 40. The exit ports 48 may be spaced around the interior passageway 42. The interior passageway 42 may be used to deliver, example, the first cement volume 34 into the containment jacket 32. The interior fill tube 28 may be disposed through the interior passageway 42 of the exterior tube 26.

Figure 12:
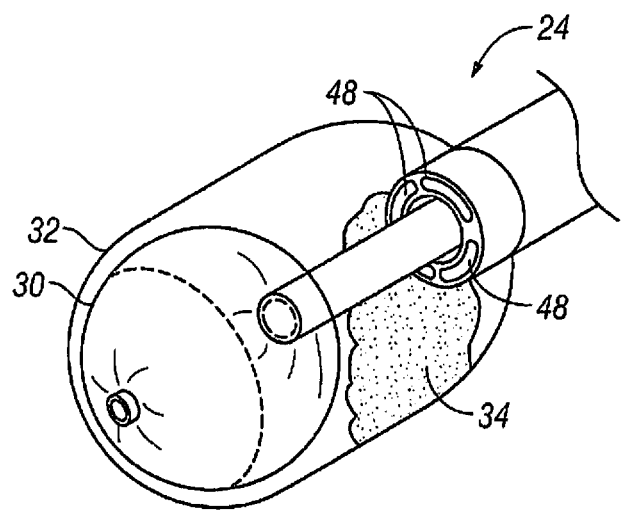
FIG. 12 illustrates employment of an inflation and containment device in accordance with one embodiment of the present invention.

FIG. 12 illustrates employment of the inflation and containment device 24 in accordance with one embodiment of the present invention. As illustrated, employment of the device 24 may comprise inflating the second balloon 30 and the containment jacket 32. Embodiments of the present invention further may comprise introduction of a first cement volume 34 into the containment jacket 32. As illustrated, the first cement volume 34 may be introduced into the volume of the containment jacket 34 that is not occupied by the second balloon. The first cement volume 34 may be introduced through the exterior passageway 40 of the exterior tube 26, exiting into the containment jacket 34 from the one or more exit ports 48. A sufficient amount of the first cement volume 34, for example, may be introduced to generally fill the unoccupied portion of the containment jacket 34. The first cement volume 34 may then be allowed to cure in the containment jacket 34.

Figure 13:
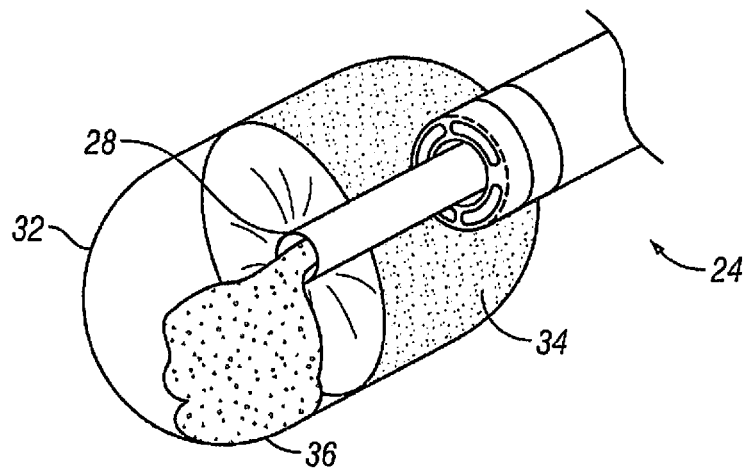
FIG. 13 illustrates further employment of an inflation and containment device in accordance with one embodiment of the present invention.

FIG. 13 illustrates further employment of the inflation and containment device 24 in accordance with one embodiment of the present invention. After the first cement volume 34 is substantially cured, for example, the second balloon 30 may be deflated and removed from the containment jacket 32. As illustrated, employment of the device 24 further may comprise introduction of the second cement volume 36 into the containment jacket 32. By way of example, the second cement volume 36 may be introduced into the space within the containment jacket 32 that was previously occupied by the second balloon 30 in an inflated state. A cement filling tube may be used to deliver the second cement volume 36 to the containment jacket 34. In certain embodiments, a sufficient amount of the second cement volume 36 may be introduced to substantially fill the remainder of the containment jacket 32. The second cement volume 36 may then be allowed to cure in the containment jacket 34.

Figure 14:
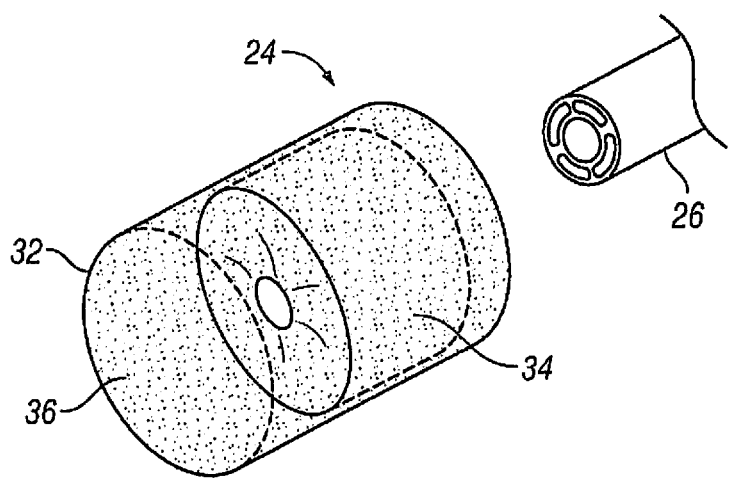
FIG. 14 illustrates yet further employment of an inflation and containment device in accordance with one embodiment of the present invention.

FIG. 14 illustrates yet further employment of the inflation and containment device 24 in accordance with one embodiment of the present invention. As illustrated, the first cement volume 34 and the second cement volume 36 generally fill the containment jacket 32. As previously mentioned, the containment jacket 32 contains the cement volumes preventing undesirable leakage. The exterior tube 26 may then be detached from the containment jacket 32, leaving the containment jacket 32 in place. It should be noted that accessing the vertebral body may be achieved through the use of a cannula or through an open access method.

The preceding description describes the use of a first cement volume 34 and a second cement volume 36 in accordance with embodiments of the present invention. Those of ordinary skill in the art will appreciate that the first cement volume 34 and the second cement volume 36 may comprise any of a variety of bone cements suitable for use in orthopedic applications. An example of a suitable bone cement comprises polymethyl methacrylate (PMMA). In addition, while the preceding description describes the use of cement, embodiments of the present invention also may encompass a variety of different filler materials that may be utilized to, for example, fill and stabilize the cavity 22 in the vertebral body 10. Examples of suitable materials may include human bone graft and synthetic derived bone substitutes.

In the exemplary embodiment, a first balloon is used to create a cavity in the vertebral body. However, any device that can be used to create cavity may be applied. For example, mechanical devices such as stents, drills, and vacuums may be used to create a cavity in the vertebral body. After the cavity is created, a containment jacket and the second balloon can be introduced according to the present invention. It should also be noted that various different methods of deploying the second balloon within the containment jacket may be used. For instance, the second balloon may be positioned in any position to maximize the efficiency and ease for inserting the cement into a particular position in the vertebral cavity.

In another exemplary embodiment of the present invention, FIGS. 15-21 illustrate a containment jacket 50 attached to a distal end of a insertion device 52. The insertion device 52 is adapted to be coupled to the containment jacket 50. The insertion device 52 is also provided with a central port 54 that is used to insert medical devices in the cavity of the vertebral body and is contained within the containment jacket 50. For instance the central port 54 can be used to insert a k-wire, endoscopic devices, bone cement and other medically compatible instrument to enhance the procedure of curing bone cement within the vertebral cavity. On opposing sides of the central port 54 and at the distal end of the central port 54, multiple balloons 56 may be attached. In different embodiments, the multiple balloons 56 may vary in size and shape. Also, on opposing sides of the central port 54 and between the insertion device walls 52, there is provided sealing elements 57. The sealing elements 57 are utilized to eliminate any risk of bone filler material or any other material being withdrawn through the insertion device 52.

A central guide wire 58 is used to initially insert the containment jacket 50 within the vertebral body. Once the containment jacket 50 is positioned within the vertebral body as illustrated in FIG. 16, the multiple balloons 56 are inserted into the cavity and inflated as illustrated in FIGS. 16 and 17. As the balloons 56 are inflated, the pressure from the outer walls of the balloons 56 inflate the containment jacket 50. After the balloons 56 are inflated to a volume that is optimal, a first filler material 60 is then inserted through the central port to a first portion within the containment jacket 50. The balloons 56 are then deflated and removed from the containment jacket through the central port. Turning now to FIGS. 18 and 19, after removal of the balloons 56, the first filler material 60 is cured, thereby providing stability and restoring height to one portion of the of the containment jacket within the vertebral body. Once the first filler material 60 is cured, a second filler material 62 may be inserted into a second portion and allowed to cure within the containment jacket 50, as shown in FIG. 20. FIG. 21 illustrates the first and second filler material being contained within the containment jacket 50. Also, the containment jacket 50 conforms to the shape of the surrounding cancellous bone and interdigitates with the surrounding bone without any leakage of the first or second filler material.

In another embodiment of the present invention, a cavity creation balloon and a height restoration balloon may be configured within a containment jacket attached to an vertebral body insertion device. In one step of the present invention, containment jacket, the cavity creation balloon and the height restoration balloon are inserted into a fractured vertebral body. Next, the cavity creation balloon and the height restoration balloon are inflated simultaneous, thereby inflating the containment jacket within the vertebral body. Once the cavity is created and the height restoration balloon is inflated, the cavity creation balloon is deflated and removed. After removal of the cavity creation balloon, a bone filler material insertion device is inserted into the containment jacket and filled with a bone filler material in a first portion of the containment jacket. Once the bone filler material is cured, the height restoration balloon is removed and a second bone filler material is inserted into the second portion of the containment jacket. Next, the second bone filler material is cured and the insertion devices are removed, leaving the containment jacket containing the first and second bone filler material in the vertebral body.

In addition, the preceding description is directed, for example, to treatment of vertebral fractures that includes an inflation device for cavity creation and an inflation and containment device for maintaining vertebral height and cement containment. It should be understood that the present technique also may be used in other suitable bone treatments were maintenance of vertebral height and/or cement containment may be desired. By way of example, embodiments of the present invention may be used to treat tibia plateau fractures, distal radius fractures, and cancellous fractures.

While it is apparent that the invention disclosed herein is well calculated to fulfill the objects stated above, it will be appreciated that numerous modifications and embodiments may be devised by those skilled in the art.

What is claimed is:

1. A method for treating a bone comprising:
   inserting a cavity creation balloon in the bone;
   inflating the cavity creation balloon in the bone to a portion of the bone and create a cavity in the bone;
   removing the cavity creation balloon from the bone;
   inserting an inflation and containment device, wherein the device comprises:
      a containment jacket;
      a fill tube comprising a distal end; and
      a second balloon within the containment jacket so that the second balloon occupies a first portion of the containment jacket, wherein the second balloon extends from the distal end of the fill tube;
   inflating the second balloon within the containment jacket;
   introducing a first filler material into a second portion of the containment jacket,
   wherein the second portion of the containment jacket is not occupied by the second balloon;
   allowing the first filler material to substantially cure;
   removing the second balloon from the first portion of the containment jacket after the first filler material has substantially cured; and
   introducing a second filler material into the first portion of the containment jacket,
   wherein the second filler material is introduced via the fill tube, and
   wherein the filler material within the containment jacket interdigitates with cancellous bone.

2. The method of claim 1, wherein the bone is a vertebral body.

3. The method of claim 1, wherein the filler material is able to interdigitate with the bone surrounding the cavity.

4. The method of claim 1, wherein the containment jacket is at least partially coated with a bone growing agent.

5. The method of claim 1, wherein the first filler material comprises a bone cement.

6. The method of claim 1, wherein the first filler material occupies from about 25% to about 75% of the volume of the cavity in the containment jacket.

7. The method of claim 1, wherein the first filler material and the second filler material are the same material.

8. The method of claim 1, wherein the first filler material and the second filler material are different materials.

9. The method of claim 1, wherein the second filler material is a bone cement.

* * * * *